US008926636B2

(12) United States Patent
Robertson et al.

(10) Patent No.: US 8,926,636 B2
(45) Date of Patent: Jan. 6, 2015

(54) DUAL OFFSET ARC NEEDLE FOR ANCHOR PLACEMENT OF A MALE INCONTINENCE SLING

(75) Inventors: David W. Robertson, Framingham, MA (US); Michael F. Weiser, Groton, MA (US); Kevin L. Newell, Jefferson, MA (US); John Petricca, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 501 days.

(21) Appl. No.: 13/074,895

(22) Filed: Mar. 29, 2011

(65) Prior Publication Data
US 2011/0306988 A1  Dec. 15, 2011

Related U.S. Application Data

(60) Provisional application No. 61/353,482, filed on Jun. 10, 2010.

(51) Int. Cl.
*A61B 17/14* (2006.01)

(52) U.S. Cl.
USPC ........... 606/139; 606/213; 606/232; 606/233; 606/190; 600/30; 600/37; 600/29; 600/31; 128/834; 128/898; 604/164.1; 434/267

(58) Field of Classification Search
USPC ........... 606/213, 230, 232, 233, 190; 600/29, 600/30, 31, 37; 604/164.1; 128/898, 834; 434/267
See application file for complete search history.

(56) References Cited

U.S. PATENT DOCUMENTS

| 5,041,127 | A | 8/1991 | Troutman |
| 5,725,555 | A | 3/1998 | Moll |
| 6,417,474 | B1 | 7/2002 | Rakus et al. |
| 6,911,003 | B2 * | 6/2005 | Anderson et al. ............... 600/30 |
| 7,364,541 | B2 * | 4/2008 | Chu et al. ......................... 600/30 |
| 7,413,540 | B2 | 8/2008 | Gellman et al. |
| 2006/0287571 | A1 * | 12/2006 | Gozzi et al. ..................... 600/30 |
| 2009/0131885 | A1 | 5/2009 | Akahoshi |

OTHER PUBLICATIONS

Bauer, et al, "Postprostatectomy Incontinence: All About Diagnosis and Management", European Urology, vol. 55, 2009, pp. 322-333.
American Medical Systems, "Expanding Treatment Options with the Next Generation of Male Sling Technology", A supplement to Urology Times, Apr. 2007, 8 pages.

* cited by examiner

Primary Examiner — Vy Q Bui
(74) Attorney, Agent, or Firm — Brake Hughes Bellermann LLP

(57) ABSTRACT

In some embodiments, an apparatus includes a handle and an elongate member coupled to the handle. The elongate member has a first portion, a second portion and a third portion. The first portion of the elongate member extends from the handle and defines a first longitudinal axis. The second portion of the elongate member extends from the first portion and defines a second longitudinal axis. The first longitudinal axis and the second longitudinal axis define a first angle and a first plane. The third portion of the elongate member extends from the second portion of the elongate member and defines a third longitudinal axis. The third longitudinal axis and the second longitudinal axis define a second angle and a second plane. The second plane is non-parallel with the first plane.

19 Claims, 10 Drawing Sheets

DUAL OFFSET ARC NEEDLE FOR ANCHOR PLACEMENT OF A MALE INCONTINENCE SLING

CROSS-REFERENCE TO RELATED APPLICATION

This application is a Nonprovisional of, and claims priority to, U.S. patent application No. 61/353,482, filed Jun. 10, 2010, entitled "DUAL OFFSET ARCH NEEDLE FOR ANCHOR PLACEMENT OF A MALE INCONTINENCE SLING," which is incorporated by reference herein in its entirety.

BACKGROUND

The disclosed embodiments relate generally to medical devices and more particularly to a medical device having a needle with multiple arcuate portions for anchor placement of a male incontinence sling into a body of a patient.

Many of the known medical devices for implanting a sling into a pelvic region of a body were developed for use in the female pelvis. The female pelvis, however, is shaped differently than the male pelvis. More particularly, in the male pelvis the angle between the inferior pubic rami is narrower (about 70 degrees) in men, and wider (about 90-100 degrees) in female pelvis. Hence, the angle is known as the subpubic angle in males and pubic arch in females. In addition the inferior rami of the pubic bone that form this angle/arch are more concave in females and straighter in males such that the male pelvis is more closed and harder to access. Thus, the shape of some known medical devices may be insufficient for reaching or maneuvering around the male pelvic bone. For example, some known medical devices include a needle defining a single plane and having an arc, thereby providing the device with only a single plane of rotation. Such known medical devices are sufficient for delivering a portion of an implant (e.g., a sling) to the obturator tissues in a female pelvis. Such known medical devices, however, can be insufficient for delivery to the obturator tissues in a male pelvis. More specifically, known medical devices having only a single plane of rotation result in the needle of the medical device running parallel to the obturator muscles instead of piercing the obturator muscles when used in male anatomy.

Thus, a need exists for a medical device that has a configuration that facilitates insertion of a sling for an implant within a male pelvic region. For example, a need exists for a medical device that facilitates insertion around or behind the male pubic bones.

SUMMARY

In some embodiments, an apparatus includes a handle and an elongate member coupled to the handle. The elongate member has a first portion, a second portion and a third portion. The first portion of the elongate member extends from the handle and defines a first longitudinal axis. The second portion of the elongate member extends from the first portion and defines a second longitudinal axis. The first longitudinal axis and the second longitudinal axis define a first angle and a first plane. The third portion of the elongate member extends from the second portion of the elongate member and defines a third longitudinal axis. The third longitudinal axis and the second longitudinal axis define a second angle and a second plane. The second plane is non-parallel with the first plane.

DETAILED DESCRIPTION

A medical device for insertion and placement of a male sling is described herein. The medical device can be inserted into a body of a patient, such as a bodily tissue, and configured to deliver an implant, such as a male incontinence sling, within the body. For example, the medical device can be used for procedures involving placing a portion of the implant near or through the obturator of the patient (e.g., via a transobturator method). In this manner, the medical device can be inserted through, into or proximate to an obturator of a male pelvis and a sling can be delivered and/or placed through, within or proximate to the obturator.

The medical device is configured to place, deposit, or otherwise insert an implant (e.g., a sling) into a bodily tissue of a patient. More particularly, the medical device is configured to be used during transobturator procedures involving the placement and insertion of a sling within a male pelvic region. The implant is configured to suspend or support a bodily tissue or organ when the implant is retained within the patient. Thus, in one embodiment, the medical device can place the implant into a pelvic obturator muscle for incontinence treatment. Specifically, a first portion of the implant and a second portion of the implant are each placed in opposing obturator muscles of a patient such that the body of the implant is extended between the first portion and the second portion to form a sling to provide support to the bulbar urethra of the patient (such a procedure is commonly referred to as "proximal bulbar relocation"). In some embodiments, however, the sling can provide support to any other suitable organ or tissue within the body. The medical device can be a variety of different configurations and can have a variety of different components, as described herein.

As used in this specification, the words "proximal" and "distal" refer to the direction closer to and further away from, respectively, an operator (e.g., surgeon, physician, nurse, technician, etc.) who would use a medical device during a procedure. For example, the end of a medical device first to contact the patient's body would be the distal end, while the opposite end of the insertion device (e.g., the end of the medical device being operated by the operator) would be the proximal end of the medical device.

Figure 1:
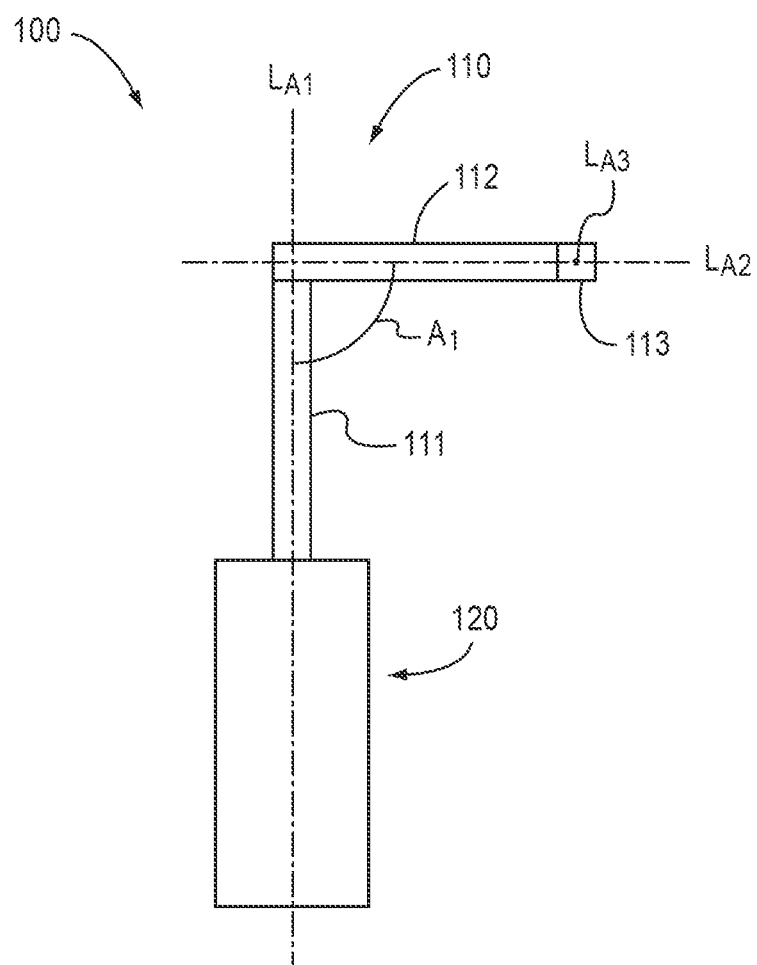
FIG. 1 is a schematic illustration of a top view of a medical device according to an embodiment.
Figure 2:
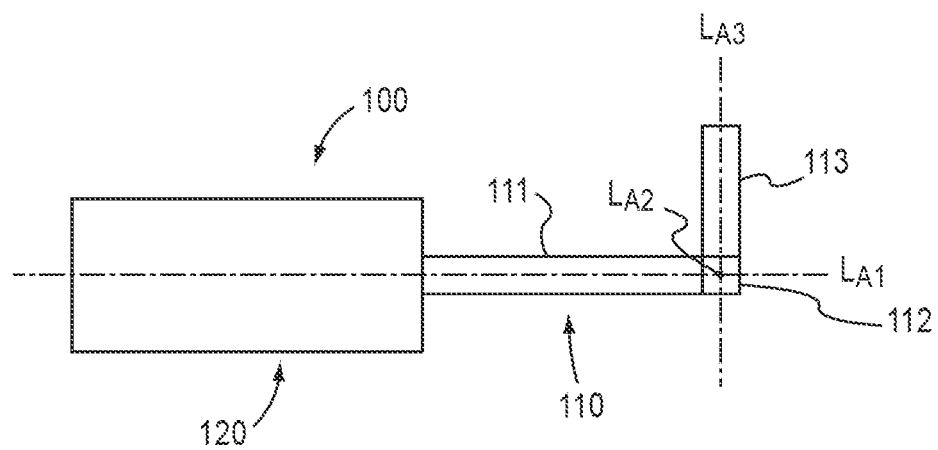
FIG. 2 is a side view of the medical device shown in FIG. 1.
Figure 3:
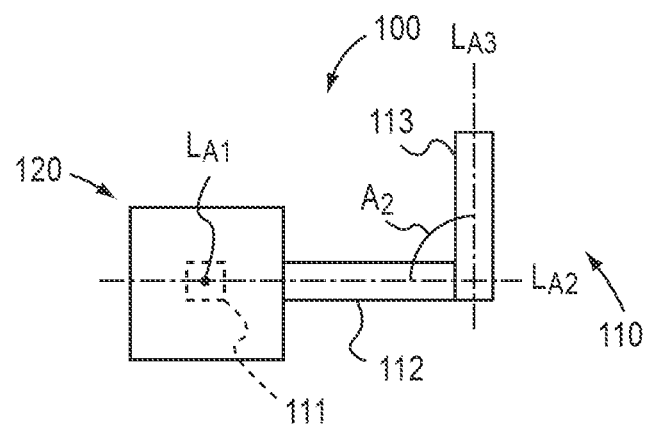
FIG. 3 is a rear view of the medical device shown in FIG. 1.

FIGS. 1-3 are schematic illustrations of a top view, a side view, and a rear view, respectively, of a medical device 100 configured to be inserted within a body of a patient. The medical device 100 includes a handle 120 and an elongate member 110 coupled to the handle 120. The elongate member 110, which can be, for example, a hypodermic needle, includes a first portion 111, a second portion 112, and a third portion 113. In some embodiments, the first portion 111, the second portion 112, and the third portion 113 have a substantially linear shape. In other embodiments, however, the first portion 111, the second portion 112 and/or the third portion 113 can have any suitable shape and/or size. In some embodiments, the first portion 111, the second portion 112 and/or the third portion 113 can be monolithically constructed. In some embodiments, the first portion 111, the second portion 112 and/or the third portion 113 can be separate pieces that are coupled together to form the elongate member 110. In some embodiments, the elongate member 110 can have more than three portions.

The first portion 111, the second portion 112, and the third portion 113 can each be of any length. In some embodiments, the first portion 111 is longer than the second portion 112 and the third portion 113. In other embodiments, the first portion 111, the second portion 112, and the third portion 113 are all of the same length. In some embodiments, each of the first portion 111, the second portion 112, and the third portion 113 are greater than 3 inches (7.6 cm). In other embodiments, each of the first portion 111, the second portion 112, and the third portion 113 are less than 3 inches (7.6 cm).

As described in more detail below, the first portion 111 of the elongate member 110 is coupled to the handle 120. The first portion 111 of the elongate member 110 extends from the handle 120 along a first longitudinal axis $L_{A1}$ defined by the first portion 111. The first portion 111, however, can extend from any other portion of the handle 120 and can extend from that portion of the handle 120 at any suitable angle, direction or manner.

The second portion 112 of the elongate member 110 extends from the first portion 111 of the elongate member 110 along a second longitudinal axis $L_{A2}$ defined by the second portion 112. The second longitudinal axis $L_{A2}$ extends from the first longitudinal axis $L_{A1}$ such that the second longitudinal axis $L_{A2}$ and the first longitudinal axis $L_{A1}$ define a first angle $A_1$ therebetween. The second portion 112 and the first portion 111 are angularly offset by the first angle $A_1$, as shown in FIG. 1. The first angle $A_1$ can be any suitable angle having any suitable magnitude. For example, in some embodiments, the first angle $A_1$ can be an obtuse angle. In other embodiments, the first angle $A_1$ can be an acute angle. In some embodiments, a curved portion can extend between the first portion 111 and the second portion 112 such that a radius of curvature can be measured between the first portion 111 and the second portion 112. The curved portion can define a radius of curvature of any suitable length. For example, the radius of curvature can be 1.0 inch, 1.1 inches, 1.5 inches, or 2 inches. In some such embodiments, the radius of curvature can be selected to blend with the adjacent portions (e.g., the first portion 111 and the second portion 112) of the elongate member 110 to ensure that the surface of the elongate member 110 is continuous. In some embodiments, the curved portion, the first portion 111, and/or the second portion 112 are monolithically constructed.

The second longitudinal axis $L_{A2}$ and the first longitudinal axis $L_{A1}$ define a first plane (not illustrated) within which the first portion 111 and the second portion 112 lie. The second portion 112 is, therefore, coplanar with the first portion 111.

The third portion 113 of the elongate member 110 extends from the second portion 112 of the elongate member 110 along a third longitudinal axis $L_{A3}$ defined by the third portion 113. The third longitudinal axis $L_{A3}$ extends from the second longitudinal axis $L_{A2}$ such that the third longitudinal axis $L_{A3}$ and the second longitudinal axis $L_{A2}$ define a second angle $A_2$ therebetween. The third portion 113 and the second portion 112 are angularly offset by the second angle $A_2$. The second angle $A_2$ can be any suitable angle having any suitable magnitude. For example, in some embodiments, the second angle $A_2$ can be an obtuse angle. In other embodiments, the second angle $A_2$ can be an acute angle. In some embodiments, the second angle $A_2$ can have a magnitude that is substantially equal to a magnitude of the first angle $A_1$. For example, in some embodiments, the second angle $A_2$ and the first angle $A_1$ can have a magnitude of approximately 90 degrees. In other embodiments, however, the magnitude of the second angle $A_2$ can be different from the magnitude of the first angle $A_1$. In yet other embodiments, a curved portion can extend between the second portion 112 and the third portion 113 such that a radius of curvature is measured between the second portion 112 and the third portion 113, as discussed above with reference to the first portion 111 and the second portion 112. In some embodiments, the curved portion, the second portion 112, and/or the third portion 113 are monolithically constructed.

The third longitudinal axis $L_{A3}$ and the second longitudinal axis $L_{A2}$ define a second plane (not illustrated). The third portion 113 and the second portion 112 lie within the second plane. Accordingly, the second longitudinal axis $L_{A2}$ lies within the first plane and the second plane. And, the second portion 112 is coplanar with the third portion 113 in the second plane and is coplanar with the first portion 111 in the first plane.

The second plane is different from, or non-parallel with, the first plane. As shown in FIG. 2, the second plane is substantially orthogonal to the first plane. The second angle $A_2$ lies within the second plane and can be any suitable angle or have any suitable magnitude, as described above, and continue to lie within the second plane. For example, the second angle $A_2$ can be an obtuse angle having a magnitude of approximately 110 degrees, and lie within the second plane which is substantially orthogonal to the first plane. In this manner, the third portion 113 is angularly offset from the second portion 112 by approximately 110 degrees and the third portion 113 and the second portion 112 lie within the second plane. Although FIGS. 2 and 3 show the third portion 113 extending from the first plane in an upward direction along the second plane, in other embodiments, the third portion 113 can extend from the first plane in any direction along the second plane.

The dual plane configuration of the medical device 100 allows the elongate member 110 to rotate about two planes (i.e., the configuration of the medical device 100 provides the elongate member 110 with two planes of rotation). The dual plane configuration can facilitate insertion of the medical device 100 (i.e., elongate member 110) around or behind an internal obstruction, such as a male pubic bone. Additionally, the dual plane configuration allows more control when delivering an implant into bodily tissue.

The third portion 113 is configured to be coupled to an implant (not illustrated), such as a mesh sling, a tissue anchor, a mesh carrier and/or the like. The third portion 113 can be coupled to the implant in any known manner. For example, in some embodiments, a distal end of the third portion 113 can be received within an opening defined by the implant such that the third portion 113 and the implant collectively form an interference fit. In some embodiments, the distal end of the third portion 113 has a sharp tip (not illustrated) configured to pierce a bodily tissue. In some embodiments, the first portion 111 and/or the second portion can be configured to couple to an implant.

The handle 120 is coupled to the first portion 111 of the elongate member 110. The handle 120 is configured to facilitate the movement of the elongate member 110 within the body of the patient. In some embodiments, the handle 120 is fixedly coupled to the first portion 111 of the elongate member 110. In other embodiments, the handle 120 is removably coupled to the first portion 111 of the elongate member 110 such that the handle 120 can be removed and re-coupled to the first portion 111 of the elongate member 110. In yet other embodiments, the handle 120 is slidably coupled to the first portion 111 of the elongate member 110 such that the handle 120 can move relative to the first portion 111, for example, along the first longitudinal axis $L_{A1}$.

The handle 120 and the first portion 111 can be coupled together by any suitable means. For example, in some embodiments, a section of the first portion 111 extends through an opening (not illustrated) defined by the handle 120 such that the first portion 111 is coupled to the handle 120 by an interference fit, a threaded coupling, and/or any like mechanical coupling. In some embodiments, the handle 120 is coupled to the first portion 111 by an electronic coupling (e.g., a magnetic coupling), and/or a chemical bond. In some embodiments, the handle 120 and the first portion 111 are monolithically constructed.

Figure 6:
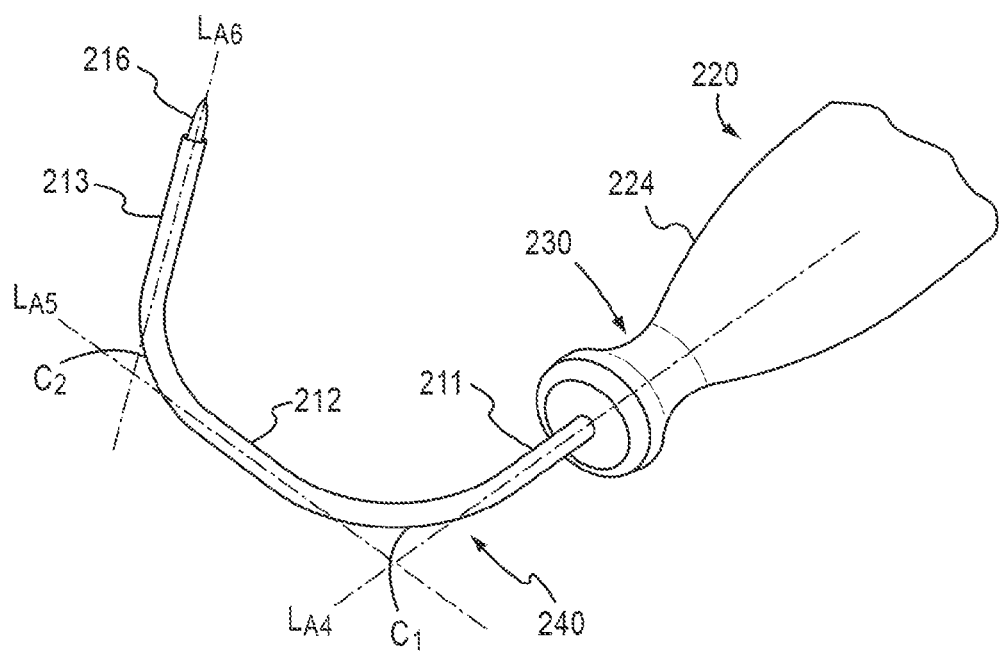
FIG. 6 is a front view of the medical device illustrated in FIG. 4.
Figure 7:
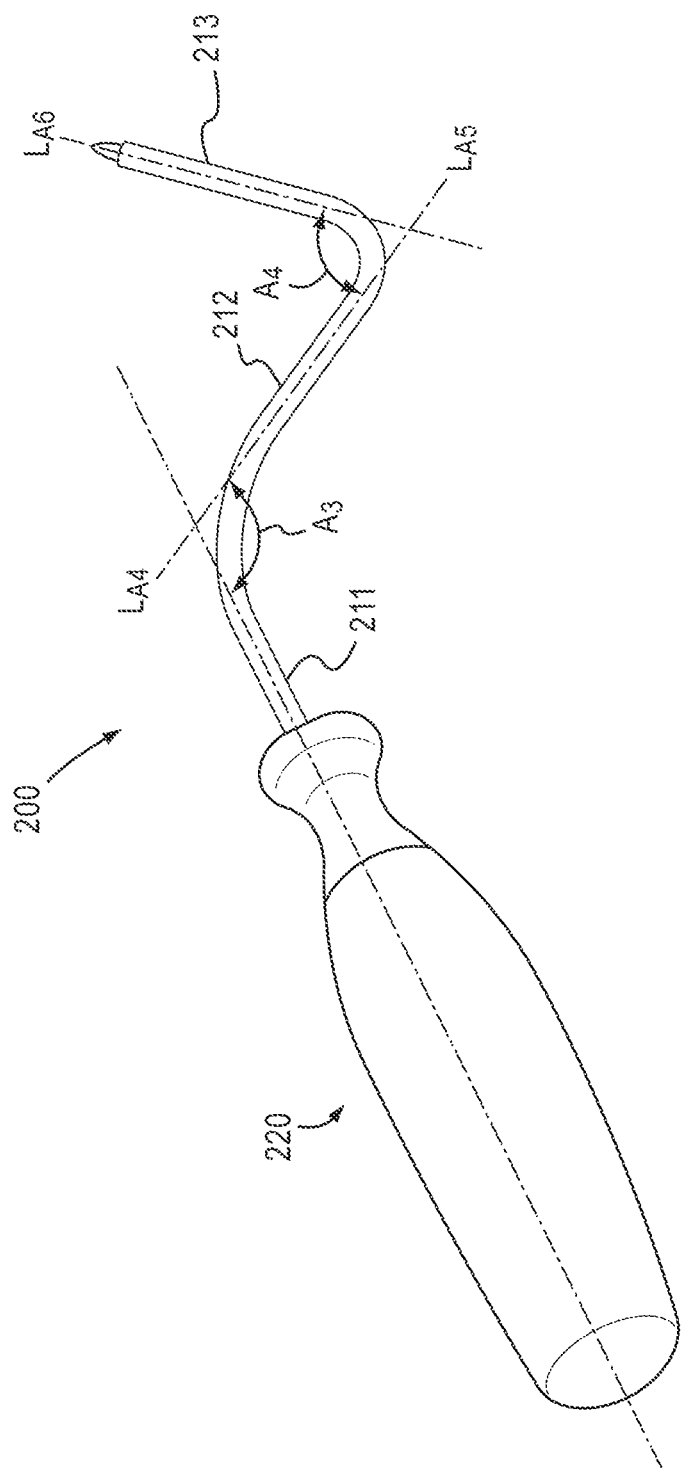
FIG. 7 is a rear view of the medical device illustrated in FIG. 4.
Figure 8:
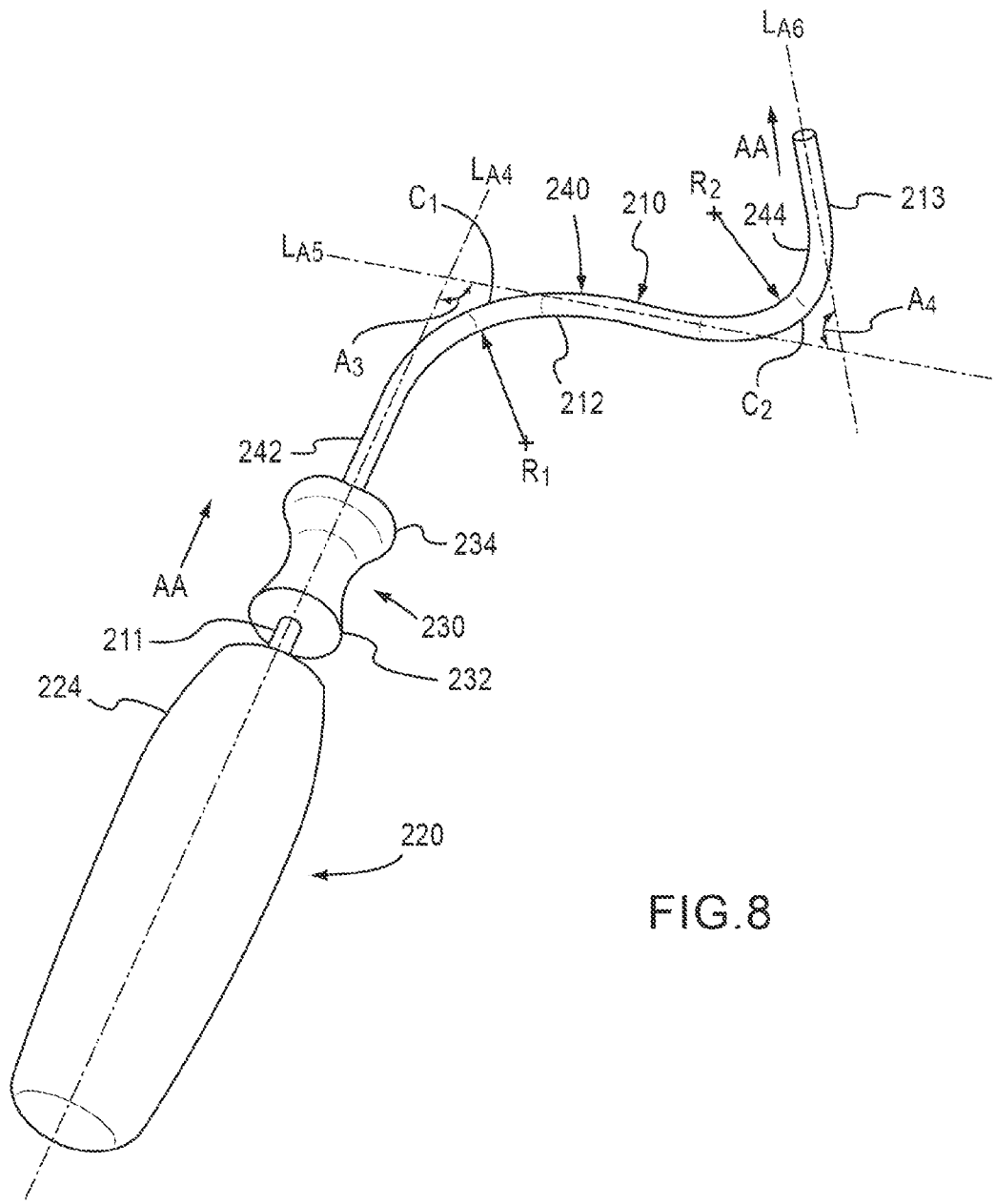
FIG. 8 is a perspective top view of the medical device illustrated in FIG. 4 in a second configuration.

FIGS. 4-7 are perspective top, side, front and rear views of a medical device 200 in a first configuration, respectively. FIG. 8 is a perspective top view of the medical device 200 in a second configuration. The medical device 200 is configured to be inserted within a body of a patient. More particularly, the medical device 200 is configured to facilitate the insertion of an implant (not illustrated) within a bodily tissue of the patient, as discussed herein. The medical device 200 includes the elongate member 210, a handle 220, an actuator 230 and a sheath 240. The elongate member 210, which can be, for example, a hypodermic needle, includes a first portion 211, a second portion 212, and a third portion 213. Although the first portion 211, the second portion 212, and the third portion 213 are illustrated as having substantially tubular shapes, in other embodiments, the first portion 211, the second portion 212 and/or the third portion 213 can have any variety of shapes, sizes, and/or configurations. In some embodiments, the first portion 211, the second portion 212 and/or the third portion 213 are monolithically constructed. In some embodiments, the first portion 211, the second portion 212 and/or the third portion 213 are separate pieces that are coupled together to form the elongate member 210. In some embodiments, the elongate member 210 includes more than three portions.

As described in more detail below, the first portion 211 of the elongate member 210 is coupled to the handle 220. The first portion 211 of the elongate member 210 extends from a distal end portion 224 of the handle 220 along a first longitudinal axis $L_{A4}$ defined by the first portion 211. The first portion 211, however, can extend from any other portion of the handle 220 and can extend from that portion of the handle 220 at any suitable angle, direction or manner.

The second portion 212 of the elongate member 210 extends angularly from the first portion 211 of the elongate member 210 along a second longitudinal axis $L_{A5}$ defined by the second portion 212. The second longitudinal axis $L_{A5}$ extends from the first longitudinal axis $L_{A4}$ such that the second longitudinal axis $L_{A5}$ and the first longitudinal axis $L_{A5}$ define a first angle $A_3$ therebetween. The first angle $A_3$ can be any suitable angle having any suitable magnitude. For example, in some embodiments, the first angle $A_3$ is an obtuse angle. In other embodiments, the first angle $A_3$ is a right angle or an acute angle.

Figure 4:
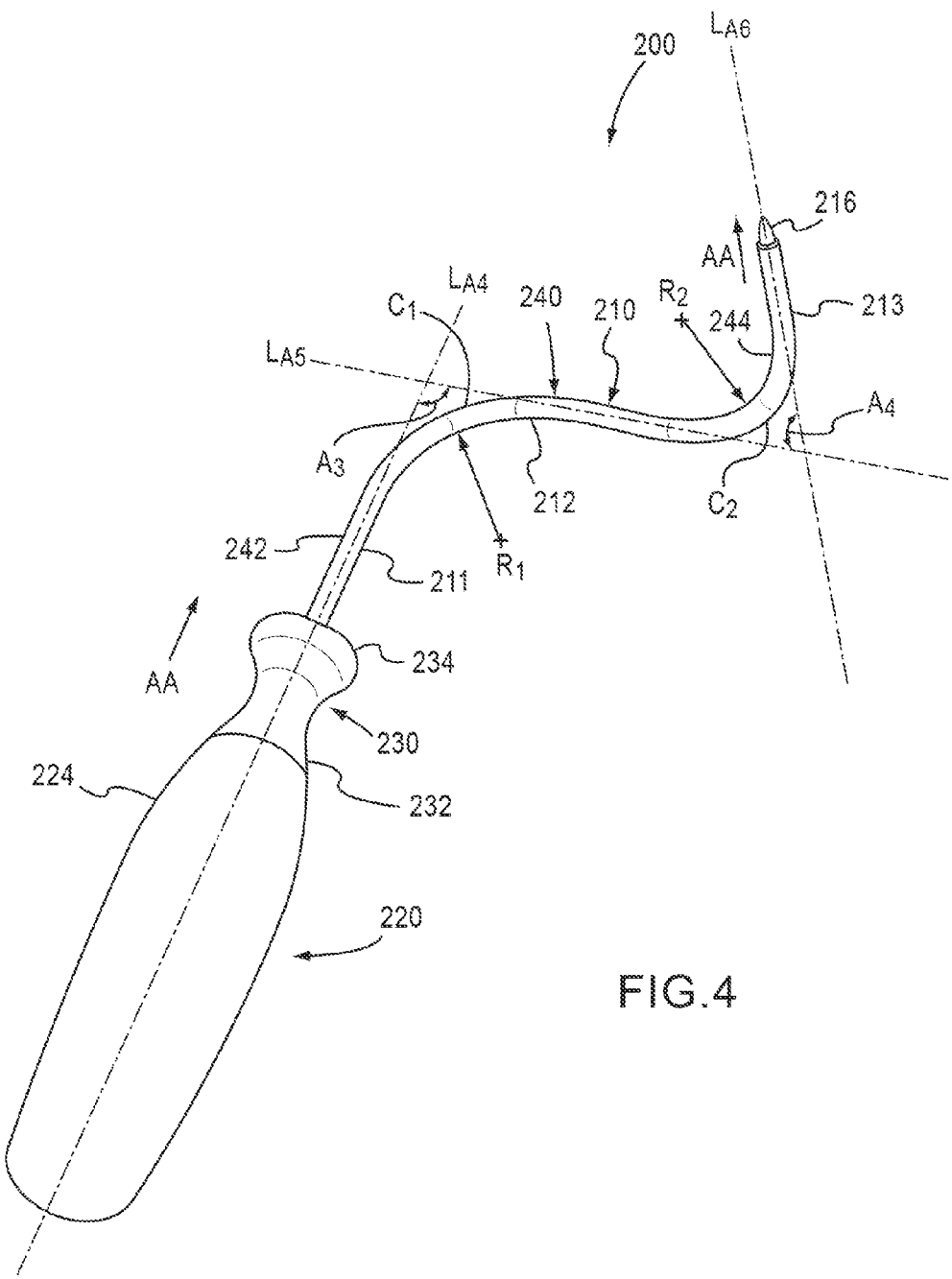
FIG. 4 is a perspective top view of a medical device in a first configuration according to an embodiment.

As shown in FIG. 4, a first curved portion $C_1$ extends between first portion 211 and the second portion 212 such that a first radius of curvature $R_1$ of the first curved portion $C_1$ corresponds to the magnitude of the first angle $A_3$. In some embodiments, however, the first curved portion $C_1$ defines a first radius of curvature $R_1$ of any suitable length. For example, the first radius of curvature $R_1$ can be 1.0 inch, 1.1 inches, 1.5 inches, or 2 inches. In some such embodiments, the first radius of curvature $R_1$ can be selected to blend with the adjacent portions (e.g., the first portion 211 and the second portion 212) of the elongate member 210 to ensure that the surface of the elongate member 210 is continuous. In some embodiments, the first curved portion $C_1$, the first portion 211, and/or the second portion 212 are monolithically constructed. Although the first curved portion $C_1$ is illustrated as being substantially arc shaped, in other embodiments, the first curved portion $C_1$ can have any suitable curvature. In some embodiments, the first curved portion $C_1$ is a portion of either the first portion 211 or the second portion 212.

The second longitudinal axis $L_{A5}$ and the first longitudinal axis $L_{A4}$ define a first plane (not illustrated) within which the first portion 211 and the second portion 212 lie. The second portion 212 is, therefore, coplanar with the first portion 211. Thus, the first angle $A_3$, the first curved portion $C_1$ and the first radius of curvature $R_1$ lie within the first plane.

The third portion 213 of the elongate member 210 extends from the second portion 212 of the elongate member 210 along a third longitudinal axis $L_{A6}$ defined by the third portion 213. The third longitudinal axis $L_{A6}$ extends from the second longitudinal axis $L_{A5}$ such that the third longitudinal axis $L_{A6}$ and the second longitudinal axis $L_{A5}$ define a second angle $A_4$ therebetween. The second angle $A_4$ can be any suitable angle having any suitable magnitude. For example, in some embodiments, the second angle $A_4$ can be an obtuse angle. In other embodiments, the second angle $A_4$ can be a right angle or an acute angle. In some embodiments, the second angle $A_4$ can have a magnitude that is substantially equal to a magnitude of the first angle $A_3$. For example, in some embodiments, the second angle $A_4$ and the first angle $A_3$ can have a magnitude of approximately 90 degrees. In other embodiments, however, the magnitude of the second angle $A_4$ can be different from the magnitude of the first angle $A_3$.

As shown in FIG. 4, a second curved portion $C_2$ extends between second portion 212 and the third portion 213 such that a second radius of curvature $R_2$ of the second curved portion $C_2$ corresponds to the magnitude of the second angle $A_4$. In some embodiments, however, the second curved portion $C_2$ defines a second radius of curvature $R_2$ of any suitable length. For example, the second radius of curvature $R_2$ can be 1.0 inch, 1.1 inches, 1.5 inches, or 2 inches. In some such embodiments, the second radius of curvature $R_2$ is selected to blend with the adjacent portions (e.g., the second portion 212 and the third portion 213) of the elongate member 210 to ensure that the surface of the elongate member 210 is continuous. In some embodiments, the second radius of curvature $R_2$ is substantially equal to the first radius of curvature $R_1$. In other embodiments, the second radius of curvature $R_2$ is different from the first radius of curvature $R_1$. In some embodiments, the second curved portion $C_2$, the second portion 212, and/or the third portion 213 are monolithically constructed. Although the second curved portion $C_2$ is illustrated as being substantially arc shaped, in other embodiments, the second curved portion $C_2$ can have any suitable curvature. In some embodiments, the second curved portion $C_2$ is a portion of either the second portion 212 or the third portion 213.

The third longitudinal axis $L_{A6}$ and the second longitudinal axis $L_{A5}$ define a second plane (not illustrated). The third portion 213 and the second portion 212 lie within the second plane. Accordingly, the second longitudinal axis $L_{A5}$ lies within the first plane and the second plane. The second portion 212 is coplanar with the third portion 213 in the second plane and is coplanar with the first portion 211 in the first plane, as described above.

Figure 5:
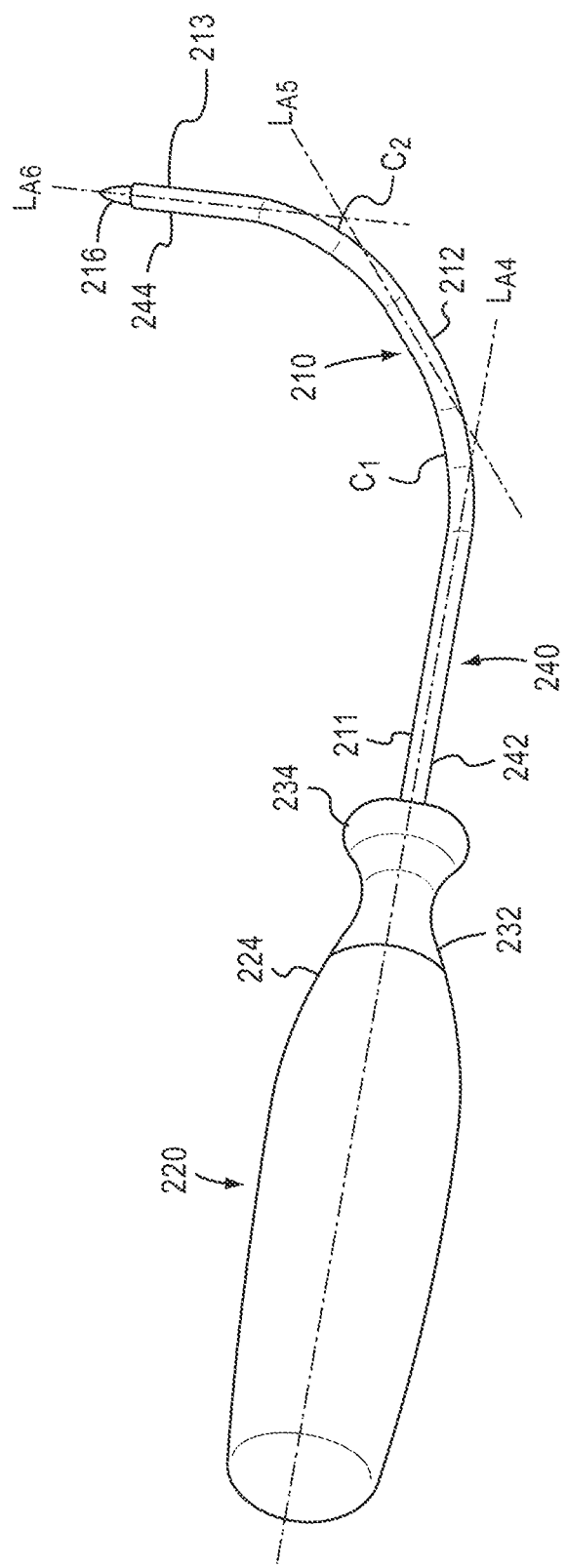
FIG. 5 is a side view of the medical device illustrated in FIG. 4.

The second plane is different from, or non-parallel with, the first plane. As shown in FIGS. 5 and 6, the second plane is substantially orthogonal to the first plane. The second angle $A_4$ lies within the second plane and can be any suitable angle or have any suitable magnitude, and continue to lie within the second plane, as described herein. Similarly, the second radius of curvature $R_2$ lies within the second plane and can have any suitable length and continue to lie within the second plane. Although FIGS. 5-7 show the third portion 213 extending from the first plane in an upward direction along the second plane, in other embodiments, the third portion 213 can extend from the first plane in any direction along the second plane. Although the second plane is described above as being substantially orthogonal to the second plane, in other embodiments, the second plane is non-normal to the first plane.

The dual plane configuration of the medical device 200 allows the elongate member 210 to rotate about two planes, as described above. The dual plane configuration and the curved portions $C_1$ and $C_2$, can facilitate insertion of the medical device 200 (i.e., the elongate member 210) around or behind an internal obstruction, such as a male pubic bone. Thus, the curved portions $C_1$ and $C_2$, in addition to the dual plane configuration allow more control when delivering an implant into bodily tissue.

The third portion 213 of the elongate member 210 includes a tip 216. The tip 216 can be a variety of shapes. For example, in some embodiments, the tip 216 is pointed. In other embodiments, however, the tip 216 is blunt or tapered. The tip 216 of the third portion 213 is configured to be removably coupled to the implant, as discussed in more detail herein. The tip 216 can be coupled to the implant in any known manner. For example, in some embodiments, the implant defines a lumen configured to receive the tip 216 of the third portion 213 such that implant and the tip 216 form an interference fit or slight frictional fit. In some embodiments, the first portion 211 and/or the second portion can be configured to couple to the implant.

The first portion 211, the second portion 212 and/or the third portion 213 of the elongate member 210 can be constructed of any material suitable for insertion into a body of a patient. For example, in some embodiments, the first portion 211, the second portion 212 and/or the third portion 213 can be constructed of stainless steel. In other embodiments, the first portion 211, the second portion 212 and/or the third portion 213 can be constructed of a polymer.

The sheath 240, which has a substantially tubular shape, is disposed about an outer surface of the elongate member 210 in a manner that allows the sheath 240 to move from a first position to a second position relative to the elongate member 210. Specifically, the sheath 240 is slidably disposed about the elongate member 210. The sheath 240 has a proximal end portion 242 and a distal end portion 244, and defines a lumen (not identified) extending therethrough. At least a portion of the elongate member 210 is disposed within the lumen defined by the sheath 240. The proximal end portion 242 of the sheath 240 is coupled to the actuator 230, as described herein. The distal end portion 244 of the sheath 240 is configured to uncouple or disengage the implant from the third portion 213 of the elongate member 210 when the sheath moves from the first position to the second position, as discussed in more detail herein.

Although the sheath 240 is illustrated and described above as having a substantially tubular shape, in other embodiments, the sheath 240 can have any variety of shapes, sizes, and configurations. The sheath 240 can be constructed of any material suitable for insertion into a body of a patient. For example, in some embodiment, the sheath 240 can be constructed of a polymer. In some embodiments, the sheath 240 can be constructed of an elastic material such that it can bend and move around the curved portions $C_1$ and $C_2$ of the elongate member 210.

The actuator 230 is slidably disposed about the first portion 211 of the elongate member 210 and configured to move between a first position and a second position relative to the elongate member 210. The actuator 230 has a distal end portion 234 and a proximal end portion 232 and defines a lumen (not identified) through which the first portion 211 of the elongate member 210 extends. The distal end portion 234 of the actuator 230 is fixedly coupled to the proximal end portion 242 of the sheath 240 such that the sheath 240 and the actuator 240 move together as a single unit between their respective first positions and second positions. More particularly, the actuator 230 is configured to move the sheath 240 between its first position and its second position relative to the elongate member 210. In this manner, the first position of the actuator 230 corresponds to the first position of the sheath 240, and the second position of the actuator 240 corresponds to the second position of the sheath 240.

The distal end portion 234 of the actuator 230 can be coupled to the proximal end portion 242 of the sheath 240 in any suitable manner. For example, the distal end portion 234 of the actuator 230 and the proximal end portion 242 of the sheath 240 can be coupled together by a mechanical coupling (e.g., an interference fit, a threaded coupling, and/or the like), an electronic coupling (e.g., a magnetic coupling), and/or a chemical bond. In some embodiments, however, the actuator 230 and the sheath 240 can be monolithically constructed. In other embodiments, the actuator 230 can be insert-molded to the sheath 240. Furthermore, the actuator 230 can be constructed of any suitable material. In one embodiment, the actuator 230 can be constructed of a polymer. For example, the actuator 230 can be constructed of acrylonitrile butadiene styrene (ABS).

The handle 220 is coupled to the first portion 211 of the elongate member 210. The handle 120 is configured to facilitate the movement of the elongate member 210 within the body of the patient. The handle 120 and the first portion 211 can be coupled together by any suitable means, as described above. For example, in some embodiments, the handle 220 and the first portion 211 can be coupled via an ultrasonic weld.

Although the handle 220 is illustrated as having a substantially cylindrical shape, in other embodiments, the handle 220 can be any suitable shape and/or size. For example, in some embodiments, the handle 220 can have a variety of shapes, sizes, and configurations, such as a contoured shape. The handle 220 can further be constructed of any suitable material. In some embodiments, the handle 220 can be constructed of at least one polymer. For example, the handle 220 can be constructed of acrylonitrile butadiene styrene (ABS). In other embodiments, the handle 220 can include a thermoplastic elastomer material (TPE) covering a portion its outer surface to provide a practitioner a comfortable or secure gripping area.

As shown in FIGS. 4-7, the medical device 200 is in the first configuration when the actuator 230 and the sheath 240 are in the first position. More specifically, when the actuator 230 is in the first position, the proximal end portion 232 of the actuator 230 abuts the handle 220. In this manner, the handle 220 is configured to restrict the collective movement of the actuator 230 and the sheath 240 in the proximal direction when the actuator 230 is in the first position. Additionally, when the sheath 240 is in the first position, the tip 216 of the third portion 213 of the elongate member 210 is disposed outside of the lumen defined by the sheath 240. In this manner, an implant can be coupled to the tip 216 of the third portion 213 when the sheath 240 is in the first position.

As shown in FIG. 8, the medical device 200 is in the second configuration when the actuator 230 and the sheath 240 are in the second position. More specifically, when the actuator 230 is in the second position, the proximal end portion 232 of the actuator 230 is disposed apart from the handle 220. Additionally, when the sheath 240 is in the second position, the tip 216 of the third portion 213 is disposed within the lumen defined by the sheath 240. Said another way, the sheath 240 substantially encloses the tip 216 of the third portion 213 when the sheath 240 is in the second position. In some embodiments, the tip 216 is completely disposed within the lumen of the sheath 240 when the sheath 240 is in the second position. In other embodiments, only a portion of the tip 216 is disposed within the lumen of the sheath 240 when the sheath 240 is in the second position. In this manner, the sheath 240 and the actuator 230 are collectively configured to decouple or otherwise disengage the implant from the tip 216 of the third portion 213 of the elongate member 210. More particularly, because the distal end portion 244 of the sheath 240 is configured to contact the implant coupled to the tip 216 of the third portion 213 when the sheath 240 is moved in the distal direction AA, it advances the implant in the distal direction AA away from the elongate member 210. This advancement disengages or decouples the implant from the tip 216 of the third portion 213 of the elongate member 210 and fixes the implant into bodily tissue.

The medical device 200 is moved from the first configuration to the second configuration when the actuator 230 is moved in distal direction AA along the elongate member 210. More particularly, the medical device 200 is moved from the first configuration to the second configuration when the actuator 230 is moved relative to the handle 220. The actuator 230 can be moved, for example, by a user applying a force on the actuator 230 in the distal direction AA (e.g., by a user pushing the actuator 230 away from the handle 220). In some embodiments, the actuator 230 maintains a constant position and the user applies a force on the handle 220 in a proximal direction (e.g., by a user pulling the handle 220 away from the actuator 230). In this manner, the elongate member 210 is moved in the proximal direction (i.e., opposite the distal direction AA) within the sheath 240.

In some embodiments, the sheath 240 and/or the actuator 230 are biased in the first position such that the medical device 200 is moved from the second configuration back to the first configuration when the user releases the actuator 230. In some embodiments, the medical device 200 is moved from the second configuration back to the first configuration, when a user applies a force on the actuator 230 and/or the sheath 240 in a proximal direction, opposite to direction AA (i.e., when a user pushes the actuator 230 and/or sheath 240 towards the handle 220).

In some embodiments, when the sheath 240 and/or the actuator 230 are moved from their respective first positions to their respective second positions (i.e., when the distal end portion 244 of the sheath 240 decouples the implant from the third portion 213 of the elongate member 210), a user can hear an audible click.

Although the third portion 213 of the elongate member 210 is described as being configured to couple to an implant such as a mesh sling, in other embodiments, the third portion 213 can be configured to couple to a carrier configured to further be coupled to an implant. In this manner, the third portion 213 of the elongate member 210 is operatively coupled to the implant via the carrier.

Figure 9:
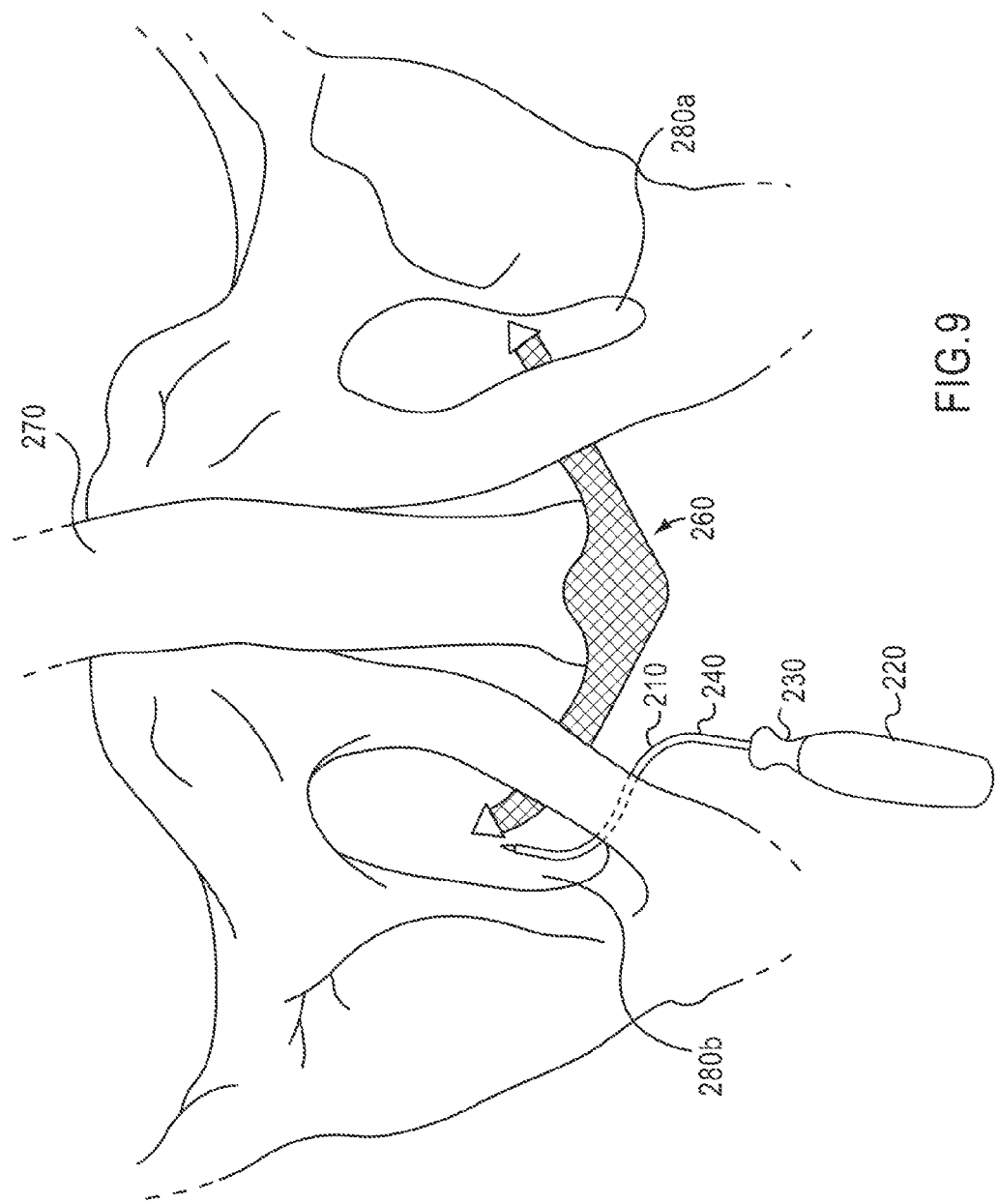
FIG. 9 illustrates a location within the male pelvic region in which a medical device can be inserted.

FIG. 9 illustrates a location within the male pelvic region within which the medical device 200 can be inserted. The medical device 200 can be inserted within the body of the patient through a transperineal incision (not illustrated) and directed toward one of the obturators 280a or 280b located within the pelvic region of the patient. When the medical device 200 is inserted into the body, the tip 216 of the elongate member 210 is coupled to one end of the implant 260 and the medical device 200 is in the first configuration.

As shown in FIG. 9, the medical device 210 punctures the obturator tissues (e.g., is inserted through the obturator foramen) from the inside of the pelvis. The curved portions $C_1$ and $C_2$ of the elongate member 210 allow the medical device 200 to maneuver around the pelvic bones. Although not clearly illustrated in FIG. 9, it should be understood that the male subpubic angle is angled inward toward the axis of the spine (i.e., less than 90 degree angle) while the female pubic arch is angled outward away from the axis of the spine (i.e., greater than 90 degree angle). Thus, the female pubis bone is more "open" and easier to access and maneuver around, and the male pubis bone is more "closed" and harder to access and maneuver around.

Once the obturator is punctured, the medical device 200 can be moved from the first configuration to the second configuration by moving the actuator 230, as described above. As a result, the end of the implant 260 is removed from the tip 216 of the elongate member 210 and is fixed within the obturator 280a or 280b. The other end of the implant 260 can then be fixed within the opposing obturator such that a portion of the implant 260 is disposed under the bulbar urethra 270. As shown in FIG. 9, the implant 260 forms a "U" shape around the bulbar urethra 270 when the ends of the implant 260 are fixed within their respective obturators 280a or 280b. In some embodiments, the medical device 200 can be used to deliver the other end of the implant 260 to the opposite obturator. In some embodiments, however, a second medical device can be used to deliver the other end of the implant 260 to the opposite obturator. Once the implant 260 is securely fixed within the body (i.e., within the obturators 280a and 280b), the medical device 200 can be removed from the body via the incision. The implant 260 remains in the body to support the bulbar urethra 270. In some embodiments, however, the implant 260 can be configured to support any organ within the body.

Figure 10:
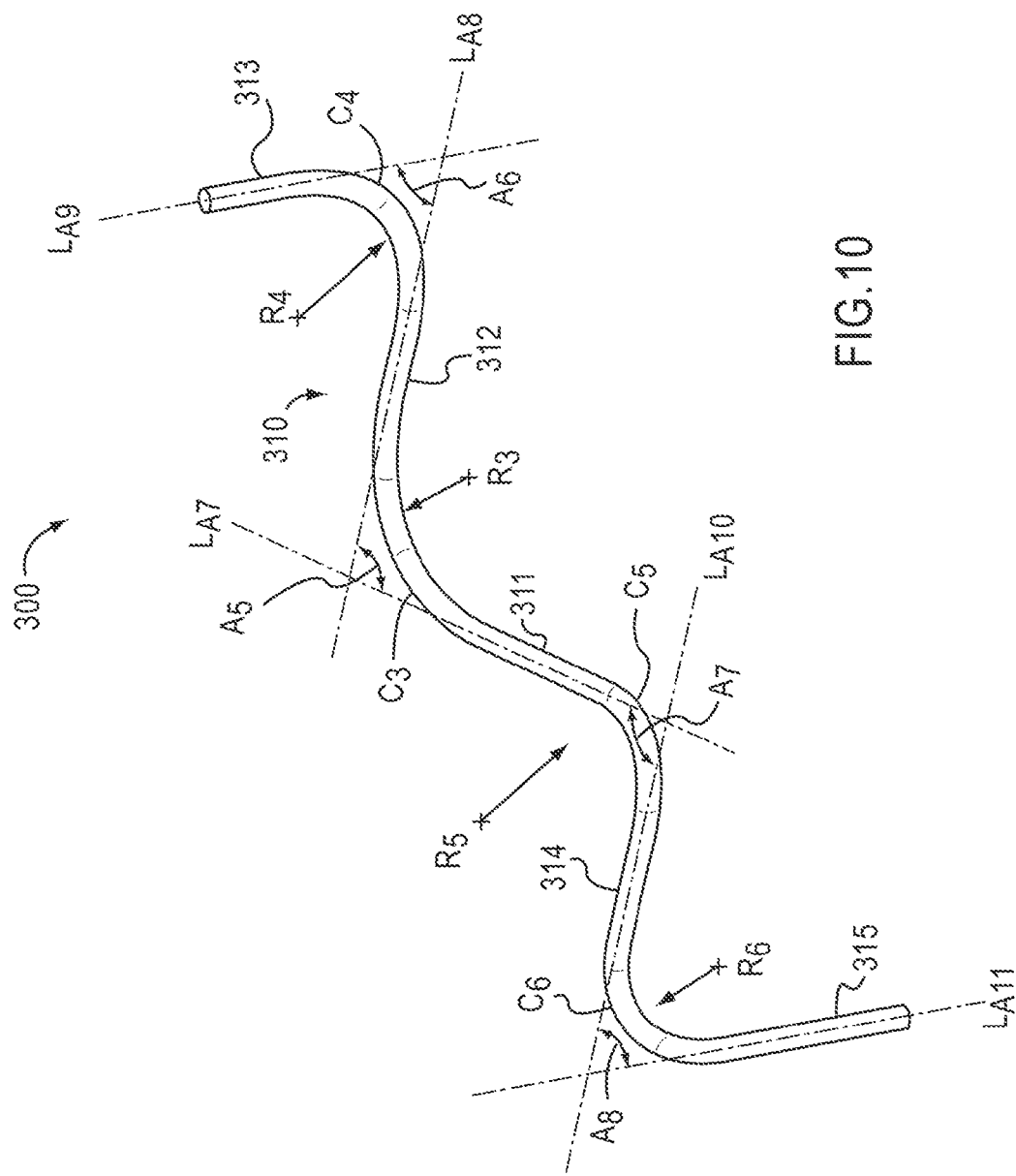
FIG. 10 is a schematic illustration of a dual-ended medical device according to an embodiment.

In some embodiments, the medical device 200 can be a dual ended medical device such that one end is configured to be used on a right obturator and the other end is configured to be used on a left obturator. For example, FIG. 10 is a schematic illustration of a dual-ended medical device 300. The medical device 300 is configured to be inserted within a body of a patient. The medical device 300 includes an elongate member 310 having a first portion 311, a second portion 312, a third portion 313, a fourth portion 314, and a fifth portion 315. The first portion 311, the second portion 312, and the third portion 313 have substantially the same structure and operation as the first portion 111, the second portion 112, and the third portion 113 of the elongate member 110 and, thus will not be described in detail herein unless otherwise specified. Additionally, the first portion 311 and the second portion 312 lie within a first plane that is substantially the same as the first plane within which the first portion 111 and the second portion 112 of the medical device 100 lie. Similarly, the second portion 312 and the third portion 313 lie within a second plane that is substantially the same as the second plane within which the second portion 112 and the third portion 113 of the medical device 100 lie. The configuration of the first portion 311, the second portion 312 and the third portion 313 of the elongate member 310 can be used to insert an implant into, for example, a right obturator.

Unlike the first portion 111 of the elongate member 110, the first portion 311 of the elongate member 310 is not coupled to a handle (e.g., handle 120). Rather, the fourth portion 314 extends proximally from the elongate member 310. In this manner, the second portion 312 extends distally from the first portion 311 and the fourth portion 314 extends proximally from the first portion 311, as shown in FIG. 10.

The fourth portion 314 extends from the first portion 311 along a fourth longitudinal axis $L_{A10}$ defined by the fourth portion 314. The fourth longitudinal axis $L_{A10}$ extends from the first longitudinal axis $L_{A7}$ such that the fourth longitudinal axis $L_{A10}$ and the first longitudinal axis $L_{A7}$ define a third angle $A_7$ therebetween. The third angle $A_7$ can be any suitable angle having any suitable magnitude, as described herein. As shown in FIG. 10, a third curved portion $C_5$ extends between the first portion 311 and the fourth portion 314 in the same manner described above with reference to first curved portion $C_1$. The third curved portion $C_5$ can define a third radius of curvature $R_5$ of any suitable length, as described above. In some embodiments, the third curved portion $C_5$, the first portion 311, the fourth portion 314 and/or the second portion 312 are monolithically constructed.

The fourth longitudinal axis $L_{A10}$ defines a portion of the first plane along with the first longitudinal axis $L_{A7}$ and the second longitudinal axis $L_{A8}$. Therefore, the fourth portion 314, the first portion 311, and the second portion 312 may lie within the same plane and may be coplanar.

The fifth portion 315 extends from the fourth portion 314 of the elongate member 310 along a fifth longitudinal axis $L_{A11}$ defined by the fifth portion 315. The fifth longitudinal axis $L_{A11}$ extends from the fourth longitudinal axis $L_{A10}$ such that the fifth longitudinal axis $L_{A11}$ and the fourth longitudinal axis $L_{A10}$ define a fourth angle $A_8$ therebetween. The fourth angle $A_8$ can be any suitable angle having any suitable magnitude, as described herein. As shown in FIG. 10, a fourth curved portion $C_6$ extends between the fourth portion 314 and the fifth portion 315 in the same manner described above with reference to second curved portion $C_2$. The fourth curved portion $C_6$ can define a fourth radius of curvature $R_6$ of any suitable length, as described above. In some embodiments, the fourth curved portion $C_6$, the fourth portion 314, and/or the fifth portion 315 are monolithically constructed.

The fifth longitudinal axis $L_{A11}$ and the fourth longitudinal axis $L_{A10}$ define a third plane. The fifth portion 315 and the fourth portion 314 lie within the third plane. Accordingly, the fourth longitudinal axis $L_{A10}$ lies within the first plane and the third plane. And, the fourth portion 314 is coplanar with the first portion 311 in the first plane and is coplanar with the fifth portion 315 in the third plane.

The third plane is different from, or non-parallel with, the first plane and the second plane. As shown in FIG. 10, the third plane is substantially orthogonal to the first plane and, thus, substantially parallel to the second plane. The fourth angle $A_8$ lies within the third plane and can be any suitable angle or have any suitable magnitude, and continue to lie within the third plane, in the same manner the second angle $A_6$ lies within the second plane. Similarly, the fourth radius of curvature $R_6$ lies within the third plane and can have any suitable length and continue to lie within the third plane. Although FIG. 10 illustrates the fifth portion 315 extending from the first plane in a downward direction along the third plane, in other embodiments, the fifth portion 315 can extend from the first plane in any direction along the third plane. For example, in some embodiments, the fifth portion 315 extends from the first plane in an upward direction along the third plane. In this manner, the fifth portion 315 extends from the first plane in the same direction the third portion 313 extends from the first plane. Although the third plane is described above as being substantially orthogonal to the first plane and being substantially parallel to the second plane, in other embodiments, the third plane is non-normal to the first plane and/or non-parallel to the second plane.

Although the medical device 300 is illustrated and described as having three planes, it should be understood that the medical device 300 only rotates about two of the planes during insertion into the body. For example, the user can grasp the fourth portion 314 and/or the fifth portion 315 as a handle and use it to rotate the medical device 300 about the first plane and the second plane when the medical device 300 is being used to insert an implant into a left obturator (or opposing obturator). Similarly, the user can grasp the third portion 313 and/or the second portion 312 as a handle and use it to rotate the medical device 300 about the first plane and the third plane when the medical device 300 is being used to insert an implant into a right obturator (or opposing obturator). The curved portions $C_3$, $C_4$, $C_5$, and $C_6$ can further facilitate insertion of the medical device 300 (i.e., the elongate member 310) around or behind an internal obstruction, such as a male pubis bone. The configuration of the medical device 300 allows more control when delivering an implant into bodily tissue.

In some embodiments, the medical device 300 rotates about each of the three planes during insertion into the body.

Similar to the third portion 313, the fifth portion 315 can be configured to be coupled to an implant (not illustrated) such as a mesh sling or a tissue anchor. The fifth portion 315 can be coupled to the implant in any known manner. In some embodiments, the distal end of the fifth portion 315 can have a sharp tip (not illustrated) configured to pierce a bodily tissue and/or couple to an implant.

In some embodiments, the medical device 300 can include a handle (not illustrated). For example, in some embodiments, the handle can be a flexible and/or soft handle configured to be removably coupled to any one of the portions 311, 312, 313, 314 and/or 315. For example, the handle can be configured to be coupled to the third portion 313 of the elongate member 310 when the fifth portion 315 is being used to deliver a first end of an implant to, for example, a right obturator. Once the delivery is complete, the handle can be removed from the third portion 313 and couple to the fifth portion 315 such that the third portion 313 can be used to deliver a second end of the implant to, for example, a left obturator.

In some embodiments, a handle can be slidably coupled to the elongate member 310. For example, in some embodiments, the handle can define a lumen through which the elongate member 310 extends. In this manner, the handle can be moved along the outer surface of the elongate member 310 from the fifth portion 315 to the third portion 313. Thus, the handle can be slid to the fifth portion 315 when the third portion 313 is being used, and can be slid to the third portion 313 when the fifth portion 315 is being used.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

Although the medical devices were illustrated and described above as having two radii of curvature (i.e., the first radius of curvature and the second radius of curvature), in other embodiments, a medical device can have any number of radii of curvatures. For example, in some embodiments, a medical device can have more than two radii of curvature. In other embodiments, a medical device can have a single radius of curvature.

In some embodiments, an apparatus includes a handle and an elongate member coupled to the handle. The elongate member has a first portion, a second portion and a third portion. The first portion of the elongate member extends from the handle and defines a first longitudinal axis. The second portion of the elongate member extends from the first portion and defines a second longitudinal axis. The first longitudinal axis and the second longitudinal axis define a first angle and a first plane. The third portion of the elongate member extends from the second portion of the elongate member and defines a third longitudinal axis. The third longitudinal axis and the second longitudinal axis define a second angle and a second plane. The second plane is non-parallel with, or different than, the first plane.

In some embodiments, the first angle and/or the second angle can be an obtuse angle.

In some embodiments, the first angle can have a magnitude that is substantially the same as a magnitude of the second angle.

In some embodiments, the handle can be slidably coupled and/or removably coupled to the elongate member.

In some embodiments, the elongate member and the handle can be monolithically constructed.

In some embodiments, the elongate member can have a sharp distal end portion.

In some embodiments, the elongate member can be a hypodermic needle.

In some embodiments, a curved portion is disposed between the first portion and the second portion, the curved portion can define a first radius of curvature disposed within the first plane.

In some embodiments, the elongate member can have a fourth portion that extends from the third portion and defines a fourth longitudinal axis. In some such embodiments, the fourth longitudinal axis and the fourth longitudinal axis can define a third angle. The fourth longitudinal axis and the third longitudinal axis can also define a third plane, which is non-parallel with, or different from, the second plane and/or the first plane.

In some embodiments, the elongate member can be configured to facilitate the delivery of an implant into at least a portion of an obturator in a male pelvis.

In some embodiments, the apparatus can include a sheath that is slidably disposed about at least a portion of the elongate member. The sheath can be configured to move, for example, from a first position to a second position.

In other such embodiments, the sheath can be configured to remove a tissue anchor coupled to the third portion of the elongate member when the sheath is moved from the first portion to the second position.

In some embodiments, a medical device includes an elongate member having a first portion, a second portion and a third portion. The second portion of the elongate member extends from the first portion of the elongate member at a first angle. The first portion and the second portion define a first plane. The third portion of the elongate member extends from the second portion of the elongate member at a second angle. The third portion and the second portion define a second plane, which is non-parallel with, or different than, the first plane. The third portion has a receiving portion that is configured to be removably coupled to a tissue anchor.

In some embodiments, the second plane can be non-normal to the first plane.

In some embodiments, the first angle and/or the second angle can be an obtuse angle.

In some embodiments, the first angle has a magnitude that can be substantially the same as a magnitude of the second angle.

In some embodiments, the first portion and the second portion can collectively provide a first plane of rotation, and the second portion and the third portion can collectively provide a second plane of rotation.

In some embodiments, the elongate member can be a hypodermic needle.

In some embodiments, the first portion, the second portion and/or the third portion of the elongate member can be monolithically constructed.

In some embodiments, the elongate member can have a fourth portion and a fifth portion. The fourth portion, which is disposed within the first plane, can extend from the first portion at a third angle. Similarly, the fifth portion can extend from the fourth portion at a fourth angle. In some such embodiments, the fourth portion and the fifth portion can define a third plane, which is non-parallel with, or different from, the first plane and/or the second plane.

In some embodiments, the medical device can include a sheath that is slidably disposed about at least a portion of the elongate member. In some such embodiments, the sheath can be configured to move from a first position to a second position.

In other such embodiments, the sheath can be configured to remove a tissue anchor coupled to the third portion of the elongate member when the sheath is moved from the first portion to the second position.

In some embodiments, the elongate member can be configured to facilitate the delivery of an implant into at least a portion of an obturator in a male pelvis.

The previous description of the embodiments is provided to enable any person skilled in the art to make or use the invention. While the invention has been particularly shown and described with reference to embodiments thereof, it will be understood by those skilled in art that various changes in form and details may be made.

What is claimed is:

1. An apparatus, comprising:
a handle;
an elongate member coupled to the handle, the elongate member having a first portion, a second portion and a third portion,
the first portion extending from the handle and defining a first longitudinal axis,
the second portion extending from the first portion and defining a second longitudinal axis, the first longitudinal axis and the second longitudinal axis defining a first angle, the first longitudinal axis and the second longitudinal axis defining a first plane, the third portion extending from the second portion and defining a third longitudinal axis, the third longitudinal axis and the second longitudinal axis defining a second angle, the second longitudinal axis and the third longitudinal axis defining a second plane, the first plane and the second plane being non-parallel, the first angle having a magnitude that is substantially the same as a magnitude of the second angle;

a sheath slidably disposed about at least a portion of the first portion, the second portion, and at least a portion of third portion of the elongate member.

2. The apparatus of claim 1, wherein each of the first angle and the second angle is an obtuse angle.

3. The apparatus of claim 1, wherein the handle is removably coupled to the elongate member.

4. The apparatus of claim 1, wherein the elongate member and the handle are monolithically constructed.

5. The apparatus of claim 1, wherein the elongate member has a sharp distal end portion.

6. The apparatus of claim 1, wherein a curved portion is disposed between the first portion and the second portion, the curved portion defines a radius of curvature disposed within the first plane.

7. The apparatus of claim 1, wherein the elongate member has a fourth portion extending from the third portion and defining a fourth longitudinal axis, the fourth longitudinal axis and the fourth longitudinal axis define a third angle, the fourth longitudinal axis and the third longitudinal axis defining a third plane, the third plane being non-parallel with at least one of the second plane and the first plane.

8. The apparatus of claim 1, further comprising:

an actuator coupled to the sheath, wherein the sheath is configured to move from a first position to a second position based on a movement of the actuator.

9. The apparatus of claim 8, wherein the actuator is disposed between the sheath and the handle, and the actuator is configured to move distally away from the handle thereby moving the sheath from the first position to the second position.

10. A medical device, comprising:

an elongate member having a first portion, a second portion and a third portion, the elongate member having a first curved portion disposed between the first portion and the second portion, and a second curved portion disposed between the second portion and the third portion, the second portion extending from the first portion at a first angle, the first portion and the second portion defining a first plane, the third portion extending from the second portion at a second angle, the third portion having a receiving portion, the receiving portion being configured to be removably coupled to a tissue anchor, the third portion and the second portion defining a second plane that is non-parallel with the first plane, the first angle having a magnitude that is substantially the same as a magnitude of the second angle; and a sheath slidably disposed about at least a portion of the first portion, the second portion, and at least a portion of the third portion of the elongate member.

11. The medical device of claim 10, wherein the second plane is non-normal to the first plane.

12. The medical device of claim 10, wherein at least one of the first angle and the second angle is an obtuse angle.

13. The medical device of claim 10, wherein the first portion and the second portion collectively provide a first plane of rotation, and the second portion and the third portion collectively provide a second plane of rotation.

14. The medical device of claim 10, wherein the first portion, the second portion and the third portion of the elongate member are monolithically constructed.

15. The medical device of claim 10, wherein the elongate member has a fourth portion and a fifth portion, the fourth portion extends from the first portion at a third angle, the fourth portion is disposed within the first plane, the fifth portion extends from the fourth portion at a fourth angle, the fourth portion and the fifth portion defining a third plane that is non-parallel with at least one of the first plane and the second plane.

16. The medical device of claim 10, further comprising:

an actuator coupled to the sheath, wherein the sheath is configured to move from a first position to a second position based on a movement of the actuator.

17. The medical device of claim 16, wherein the actuator is disposed between the sheath and the handle, and the actuator is configured to move distally away from the handle thereby moving the sheath from the first position to the second position.

18. The medical device of claim 10, wherein the elongate member is configured to facilitate the delivery of an implant into at least a portion of an obturator in a male pelvis.

19. The medical device of claim 10, wherein the radius of curvature of the first curved portion corresponds to the radius of curvature of the second curved portion.

* * * * *